United States Patent
Berkman

(10) Patent No.: US 7,073,374 B2
(45) Date of Patent: Jul. 11, 2006

(54) SOIL COMPACTION MEASUREMENT ON MOVING PLATFORM

(75) Inventor: Evan F. Berkman, Newton Center, MA (US)

(73) Assignee: BBNT Solutions LLC, Cambridge, MA (US)

( * ) Notice: Subject to any disclaimer, the term of this patent is extended or adjusted under 35 U.S.C. 154(b) by 0 days.

(21) Appl. No.: 10/901,639

(22) Filed: Jul. 29, 2004

(65) Prior Publication Data

US 2005/0022585 A1 Feb. 3, 2005

Related U.S. Application Data

(60) Provisional application No. 60/491,180, filed on Jul. 30, 2003.

(51) Int. Cl.
*B23Q 17/20* (2006.01)
(52) U.S. Cl. ........................................................ 73/78
(58) Field of Classification Search ..................... 73/78
See application file for complete search history.

(56) References Cited

U.S. PATENT DOCUMENTS

| | | | |
|---|---|---|---|
| 1,871,756 A | 8/1932 | Spath | 73/594 |
| 3,224,253 A | 12/1965 | McKay | 73/594 |
| 3,362,216 A | 1/1968 | Hardin et al. | 73/594 |
| 3,427,877 A | 2/1969 | Swift et al. | 73/146 |
| 3,481,183 A | 12/1969 | Swift | 73/573 |
| 3,643,498 A | 2/1972 | Hardin | 73/594 |
| 3,693,513 A * | 9/1972 | Borsutzki et al. | 404/117 |
| 3,778,177 A * | 12/1973 | Haker et al | 73/654 |
| RE27,875 E | 1/1974 | Swift | 73/67.1 |
| 3,795,286 A | 3/1974 | Meyer | 73/594 |
| 3,813,929 A | 6/1974 | Hardin et al. | 73/784 |
| 3,863,202 A | 1/1975 | Landrum, Jr. | 73/594 |
| 3,924,451 A | 12/1975 | Drnevich | 73/67.2 |
| 3,946,598 A | 3/1976 | Towne et al. | 73/594 |
| 4,127,351 A * | 11/1978 | Vural | 404/72 |
| 4,149,253 A | 4/1979 | Paar et al. | 404/84 |
| 4,348,901 A | 9/1982 | Vural et al. | 73/594 |
| 4,382,384 A | 5/1983 | Mitchell et al. | 73/594 |
| 4,445,378 A | 5/1984 | Zuckerwar | 73/594 |
| 4,467,652 A | 8/1984 | Thurner et al. | |
| 4,589,288 A * | 5/1986 | Porter et al. | 73/849 |
| 4,594,899 A | 6/1986 | Henke et al. | 73/784 |
| 4,655,082 A | 4/1987 | Peterson | 73/594 |
| 4,722,635 A * | 2/1988 | Schnell | 404/76 |
| 4,738,138 A | 4/1988 | Redman-White | 73/594 |
| 4,750,157 A | 6/1988 | Shei | 73/594 |
| 4,870,601 A * | 9/1989 | Sandstrom | 702/43 |
| 4,912,979 A | 4/1990 | Sondergeld et al. | 73/594 |
| 4,918,988 A | 4/1990 | Ebihara et al. | 73/594 |
| 4,995,008 A | 2/1991 | Hornbostel et al. | 73/594 |

(Continued)

OTHER PUBLICATIONS

"Compaction Monitor", Product Brochure, Gas Research Institute, Foster-Miller, Inc. and Longyear, pp. 1-3 (Jan. 18, 1994).

(Continued)

*Primary Examiner*—Max Noori
(74) *Attorney, Agent, or Firm*—Westman, Champlin & Kelly

(57) ABSTRACT

An apparatus and method are provided for the in-situ measurement of the stiffness of a surface. The apparatus includes a platform, which is movable relative to the surface. A stiffness measurement device is supported by the platform in a stationary position relative to the surface for a measurement period during movement of the platform along the surface.

20 Claims, 9 Drawing Sheets

U.S. PATENT DOCUMENTS

| | | | |
|---|---|---|---|
| 5,105,650 A | 4/1992 | Atkinson et al. | 73/594 |
| 5,398,215 A | 3/1995 | Sinha et al. | 367/31 |
| 5,804,738 A * | 9/1998 | Bach et al. | 73/849 |
| 5,892,157 A * | 4/1999 | Syre | 73/849 |
| 5,996,413 A | 12/1999 | Lyer et al. | 73/592 |
| 6,213,681 B1 | 4/2001 | Sick et al. | 404/133.05 |
| 6,260,409 B1 | 7/2001 | Briaud et al. | 73/86 |
| 6,289,734 B1 | 9/2001 | Daugela | 73/573 |
| 6,366,537 B1 | 4/2002 | Sambuelli et al. | 367/178 |
| 6,431,790 B1 | 8/2002 | Anderegg et al. | 404/75 |
| 6,604,432 B1 | 8/2003 | Hamblen et al. | 73/784 |

OTHER PUBLICATIONS

"Field Computer-CCS-RA Compaction Meter", Product Brochure, Dynapac Heavy Equipment AB, pp. 1-4 (Jul. 13, 1993).

"Measurement of the Degree of Compaction by the Impedance Method", T. Tamura and T. Sakai, Journal of Terramechanics, pp. 125-135 (Jan. 1992).

* cited by examiner

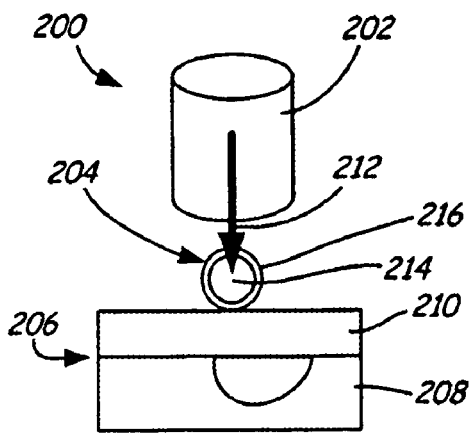
FIG. 13
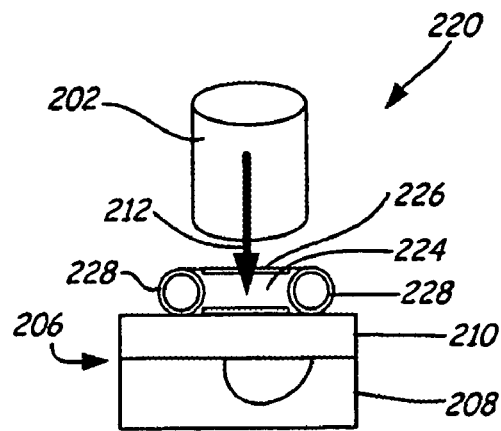
FIG. 14
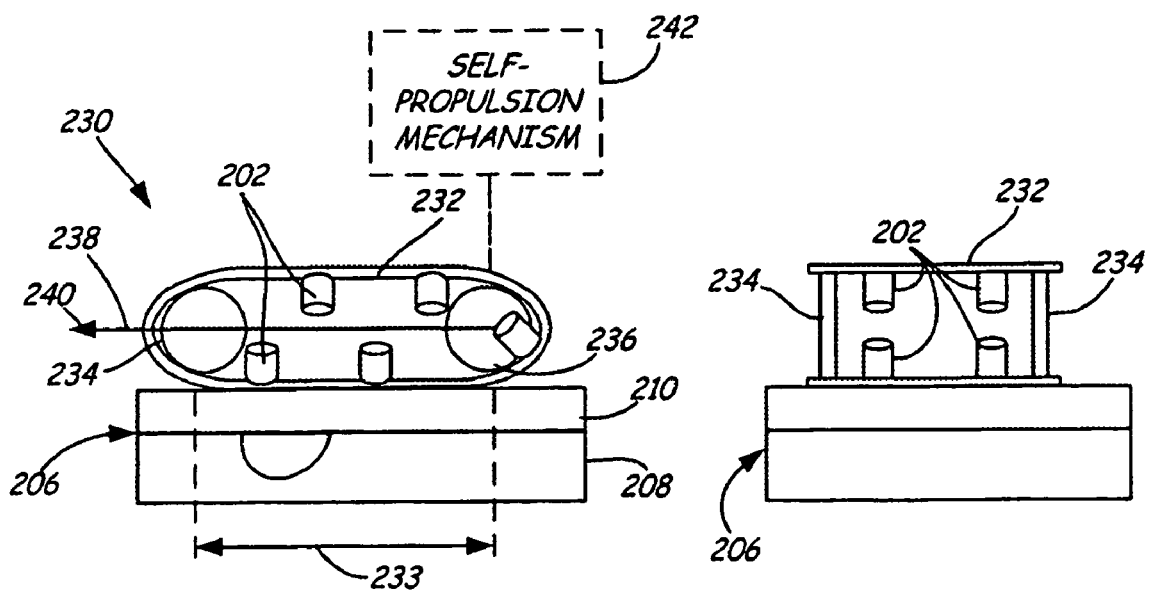
FIG. 15
FIG. 16

SOIL COMPACTION MEASUREMENT ON MOVING PLATFORM

CROSS-REFERENCE TO RELATED APPLICATIONS

The present application claims priority from and the benefit of U.S. Provisional Application No. 60/491,180, filed Jul. 30, 2003.

Cross-reference is also made to related U.S. application Ser. No. 10/461,140, filed Jun. 13, 2003 and entitled "Soil Compaction Measurement."

FIELD OF THE INVENTION

The present invention relates to the measurement of the properties on the surface of a large body of material, such as soil or compacted asphalt, and more particularly to an apparatus for measuring soil or asphalt compaction properties from a moving platform. The invention can also be used to measure the stiffness of other ground surfaces (such as concrete pavements and reinforced soils) and thereby infer the elastic properties of these surfaces and assess their state of structural integrity (for example, the presence of voids under pavements or delamination of steel reinforcement bars in concrete pavements).

BACKGROUND OF THE INVENTION

As is understood, soil is an important building material. It serves as the base for virtually all pavements, tunnels and buildings, and thus, can be thought of as an element used in construction. In construction, soil will typically be specified to have certain minimal mechanical properties, e.g., dry density, resilient modulus and strength. While some testing can be conducted in a laboratory, e.g., to determine the suitability of a raw material or blend of materials, it is also typical to perform field tests to assess the soil selection or composition, to determine appropriate site-specific compaction specifications, and to monitor for in-process quality control of the degree of compaction that affects mechanical properties of interest, typically a specified void (as reflected in density) ratio or resilient modulus.

As is understood by those skilled in the art, soil used to fill or level a construction site must be compacted, typically by the application of vibratory energy and weight, in order to obtain the requisite density and modulus. Sometimes, contractors over-compact soil as each of successive layers are added in order to ensure that the result will meet the requisite specification when completed. The ability to quickly and reliably test soil properties could significantly reduce costs due to unnecessary over-compaction and avoid long-term settlement problems due to spatially non-uniform compaction.

U.S. Pat. No. 6,604,432 discloses a "Soil Compaction Measurement" wherein a man-portable device characterizes the stiffness and inferred modulus of the soil over the recently compacted ground. The device excites the ground by a dynamic force supplied by a "shaker" and then measures the applied excitation force and the motion of the ground in response to the applied force. Appropriate processing is used to derive ground stiffness and inferred modulus of the material under the measurement instrument. In order to conduct a survey over a large area of recently compacted soil with this device, individual measurements must be made at many representative points. This can consume a significant amount of time depending upon the size of the area being surveyed.

Improved soil compaction measurement devices are therefore desired, which facilitate the measurement of soil compaction over an extended area.

SUMMARY OF THE INVENTION

One embodiment of the present invention is directed to an apparatus for the in-situ measurement of the stiffness of a surface. The apparatus includes a platform, which is movable relative to the surface. A stiffness measurement device is supported by the platform in a stationary position relative to the surface for a measurement period during continuous movement of the platform along the surface.

Another embodiment of the present invention is directed to an apparatus including a platform, which is movable relative to the surface. A rigid shoe is supported by the platform and has an external rolling belt that travels along a closed-loop path and has an elongated segment for engaging the surface. A stiffness measurement device generates a dynamic force and is mounted to the rigid shoe such that the dynamic force is applied to the surface through the rigid shoe and the rolling belt. The device receives a dynamic response from the surface through the rigid shoe and the rolling belt.

Another embodiment of the present invention is directed to a method of making an in-situ measurement of the stiffness of a surface. The method includes: (a) moving a platform relative to the surface; (b) carrying a stiffness measurement device on the platform; (c) supporting the stiffness measurement device in a stationary position relative to the surface for a measurement period during movement of the platform along the surface; (d) applying a vibratory force from the stiffness measurement device to the surface; and (e) sensing motion of the surface in response to the vibratory force and generating a respective measurement signal, which is representative of the surface stiffness.

Another embodiment of the present invention is directed to an apparatus for the in-situ measurement of the stiffness of a surface. The apparatus includes a platform, a roller and a stiffness measurement device. The platform is movable relative to the surface. The roller is supported by the platform for engaging the surface. The stiffness measurement device generates a dynamic force and is mounted to the roller such that the dynamic force is applied to the surface through the roller, and the device receives a dynamic response from the surface through the roller. The device includes a set of one or more sensors, the set having an output representative of the dynamic force applied to the roller and an output representative of the dynamic response of the surface.

BRIEF DESCRIPTION OF THE DRAWINGS

FIG. 13 is a schematic view of a moving platform on which a compaction measurement instrument is mounted on one or more rolling wheels for contacting and moving over the ground, according to an alternative embodiment of the present invention.

FIG. 14 is a schematic view of a moving platform having a rolling belt, according to an alternative embodiment of the present invention.

FIG. 15 is a schematic diagram of a tracked vehicle platform, according to an alternative embodiment of the present invention.

FIG. 16 is front-end view of the platform shown in FIG. 15.

Corresponding reference characters indicate corresponding parts throughout the several views of the drawings.

DETAILED DESCRIPTION OF ILLUSTRATIVE EMBODIMENTS

One embodiment of the present invention is directed to a method and apparatus for making soil property measurements, such as measurements of soil modulus, using a moving measurement instrument for "measurement while in-motion". The use of a moving measurement instrument reduces the time required to survey a large area of recently compacted soil while providing an accurate assessment of the extent of compaction. Rapid and accurate determination of the condition of the soil compaction is important for timely and cost-effective construction.

A wide variety of different types of soil compaction devices can be adapted for use on a moving platform or other vehicle to form a moving measurement instrument in accordance with the present invention. In one embodiment, compaction measurement device such as that disclosed in U.S. Pat. No. 6,604,432 is used on a movable platform, which automatically moves the device to various points on recently compacted soil. The device is further modified to include a means for locating the points where the measurements are made and a means for logging both the locations and the measured stiffness and/or inferred modulus values. With this particular device, the device excites the ground with a dynamic force supplied by a motion generation source (a "shaker"), measures the applied excitation force and the motion of the ground in response to the applied force, and then processes these measurements to derive ground stiffness and inferred modulus of the material under the device.

The platform or transport means can be a vehicle such as a tracked vehicle, a tractor, a truck or an all terrain vehicle that employs a suitable integral platform or a towed platform that holds the measurement device(s) in contact with the ground.

Figure 1:
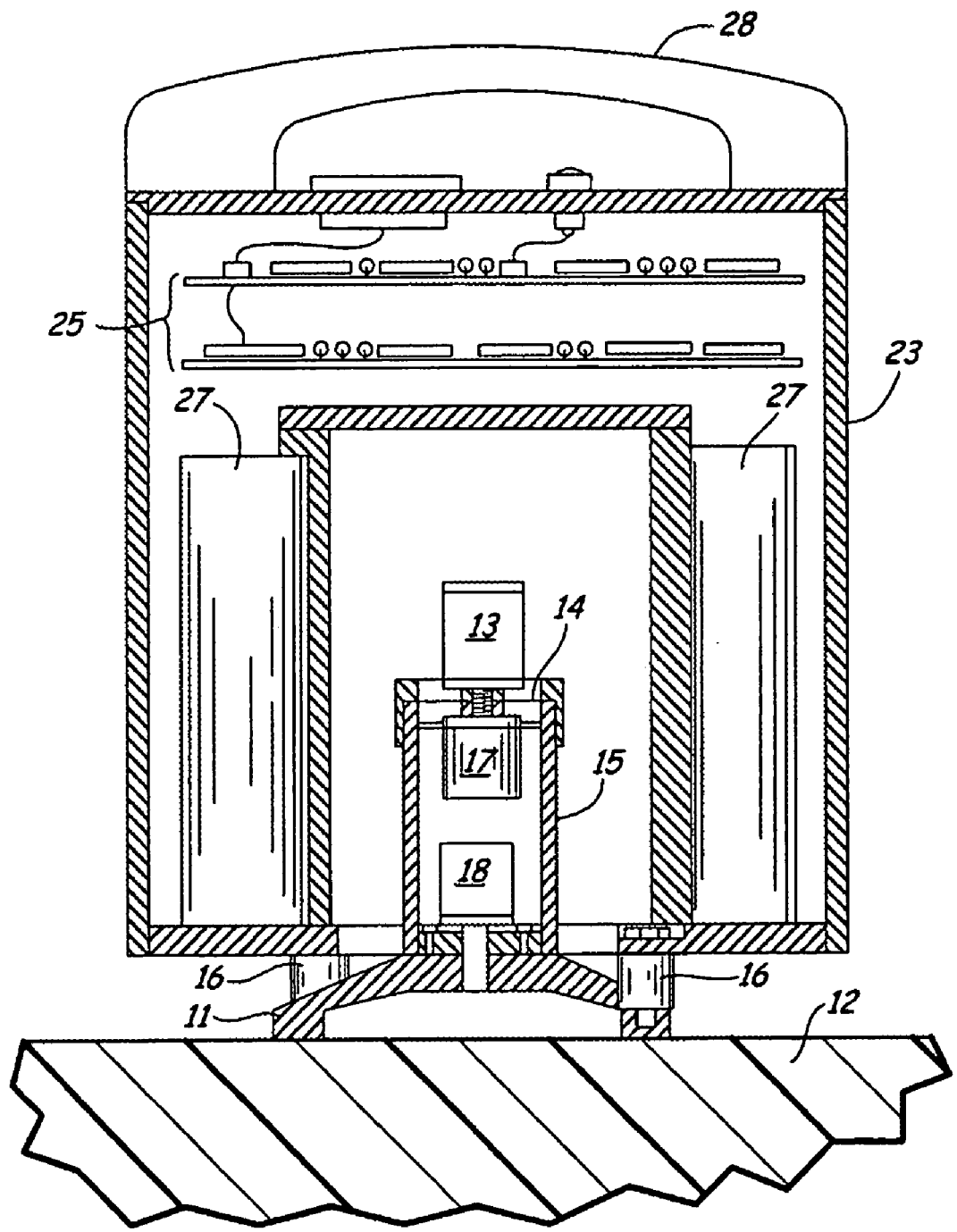
FIG. 1 is a side view of a measurement apparatus in accordance with one embodiment of the present invention.

1. Example of a Soil Copmaction Measurement Device that can be Adapted for Measurement in Motion FIGS. 1–12 illustrate the soil compaction measurement device disclosed in U.S. Pat. No. 6,604,432. FIG. 1 is a cross-sectional view of the device, which is intended to be man portable so that a worker can easily move it from location to location within a construction site. The apparatus is designed to stand on a contact foot 11, which, as is described in greater detail hereinafter, engages a defined surface area or region of soil (or other surface, such as asphalt or other pavements) 12 to be tested. The effective depth of measurement of the apparatus is on the order of 1 to 2 times the nominal diameter. In the example embodiment illustrated, the diameter of the foot is about 4½ inches as is appropriate for lifts, or fill layers, up to about 12 inches. Larger or smaller foot diameters may be appropriate in alternate embodiments for measuring soils of different characteristics, providing deeper or limiting effective depth of the measurement, measuring stiffness of other types of surfaces such as pavements, and providing a foot diameter appropriate for other selections of measurement frequency ranges. Likewise, while a circular foot is preferred, it should be understood that a non-circular contact foot member or members might also be used, such as a multiplicity of small circular pads with centers equally-spaced on a larger diameter circle.

A drive transducer, e.g., in the form of an electromechanical linear motor 13, is provided for shaking the contact foot vertically in response to drive signals applied to the transducer. The motor 13 is not connected directly to the foot 11 but rather is connected through a disk-shaped calibrated spring 14 and a cylindrical coupling 15. The output element of motor 13 is connected to the center of the spring 14. When the motor is energized with a dynamic signal, the output element moves the center of the spring, working against the inertial mass of the motor itself. While the spring 14 is circular, it is convenient in terms of force analysis and claim wording to refer to the center of the spring as its input "end" and the periphery of the spring as its output "end", since other forms of calibrated springs could be used.

A first motion sensor (e.g., a velocity sensing geophone) 17 senses the motion at the input end or center of the spring 14 while a second similar sensor (e.g., a geophone) 18 senses the resulting motion of the foot 11, which contacts the soil 12. Since the foot 11 is effectively connected rigidly through cylindrical coupling 15 to the periphery of spring 14, the second motion sensor 18 also provides a measurement of the output end of the spring. Since the stiffness of the spring 14 is predetermined or calibrated and thereby known, the force applied to the foot can be calculated from the difference in the motions (e.g., velocities) measured by the two nominally identical motion sensors 17 and 18.

As is understood by those skilled in the art, the sensors 17 and 18 may include geophones, which are moving coil velocity sensors that provide an output voltage proportional to velocity. The motor 13 can be constituted by a larger geophone with the excitation being applied to the moving coil output element, which is connected to the center of spring 14. However, motion sensors 17 and 18 can measure displacement or acceleration, rather than velocity in alternative embodiments of the present invention.

Housing 23 is mounted on the foot 11 through a set of resilient (that is, compliant) isolation mounts 16. Mounts 16 can include appropriately shaped rubber supports or other compliant mounts, such as metal coil or leaf springs. Housing carries an electronics package 25 and batteries 27, which are distributed circumferentially around the axis of the motor 13. Batteries 27 will typically constitute a substantial portion of the weight needed to provide a predetermined downward static bias force on the contact foot 11 due to the force exerted by the mass of batteries 27 under the influence of gravity. The static bias force ensures good contact with the soil and establishes an appropriate static preload stress in the soil under foot 11. If further static bias force is desired, additional inert mass may also be distributed circumferentially around the axis of the device or elsewhere in or on housing 23.

A handle 28 is provided for moving the instrument. In the example embodiment illustrated, the total weight providing a steady downward bias on the foot 11 is about 25 to 35 lbs. As will be understood, the appropriate bias weight will be roughly proportional to the area of soil surface contacted by the foot.

Figure 2:
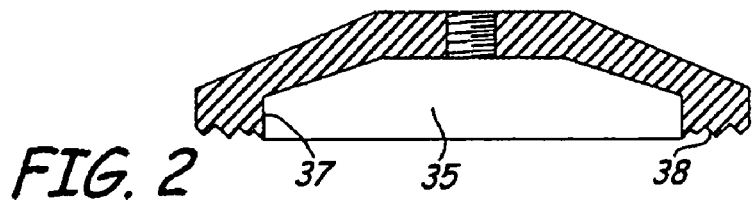
FIG. 2 is a cross-sectional illustration of a contact foot utilized in the apparatus of FIG. 1.

Referring now to FIG. 2, the foot 11 provides a recessed (e.g., arched or domed) central portion 35 and a downwardly projecting annular rim 37 which acts to control the pattern of stress on the soil to the desired distribution. The foot is preferably constructed of a light weight but rigid material, such as aluminum, since the force drop due to accelerating the mass of the foot 11 and other internal structure between the internal reference spring 14 and the ground must be effectively subtracted in order to determine the force applied to the ground and hence the ground impedance as described hereinafter. The thickness of the foot 11 and the elastic modulus of material from which it is made should be sufficiently great that the effective stiffness of the foot 11 is substantially greater (e.g., by a factor of 10 or more) than stiffness of soil or other surface to be measured. If a sufficiently large foot stiffness cannot be practically attained, then the compliance of the foot must be corrected for in computing the ground stiffness from the measured stiffness. Also, the bottom surface 38 of the annular rim 37 can be roughened; e.g., by very coarse sand paper, in order to minimize relative horizontal plane motion between the foot and the soil surfaces.

Figures 2A, 2B, 2C:
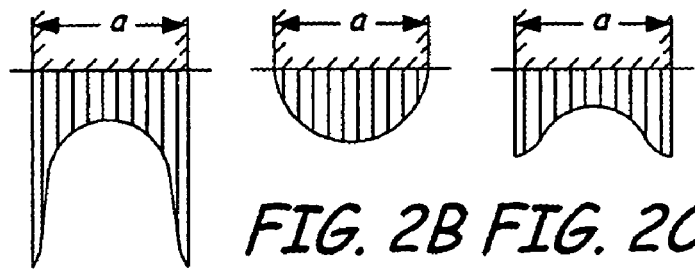
FIGS. 2A–2C are taken from Civil Engineering literature illustrating expected variability in distribution of the pressure on the base of a rigid circular foot. This variability in distribution can lead to variability in the measured stiffness. The annular contact area of the foot of FIG. 2 and of FIG. 4 was chosen to minimize this variability.

FIGS. 2A, 2B and 2C are taken from Karl Terzaghi and Ralph B. Peck, *Soil Mechanics in Engineering Practice*, John Wiley and Sons, 1967, and represent the distribution of contact pressure on base of smooth rigid footing supported by (a) real, elastic material; b) cohesionless sand; (c) soil having intermediate characteristics. These figures illustrate the motivation for the design of the annular contact area of the foot of FIG. 2. The drastic change in pressure distribution between FIGS. 2A and 2B is believed to be due to slippage between the foot's lower surface and the soil. The annular design of FIG. 2 limits the pressure distribution to an approximation of that in FIG. 2A, a preferred distribution. The rough surface shown on the bottom surface 38 of the annular rim of FIG. 2 is provided to further limit the slippage mechanism.

Figure 3:
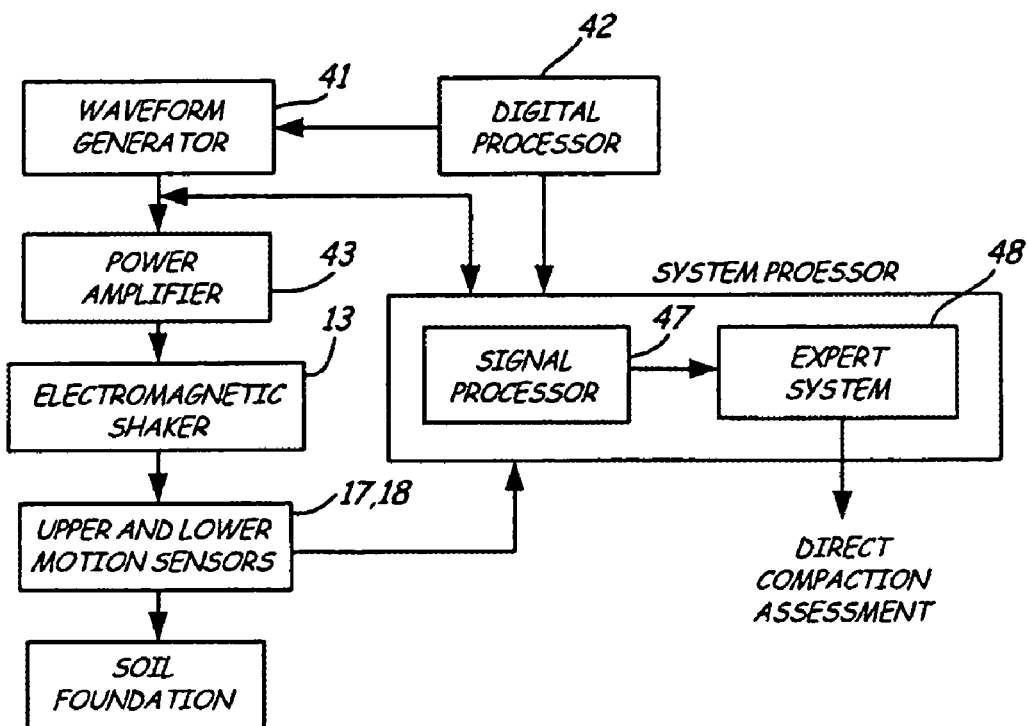
FIG. 3 is a block diagram of drive, sensing and analysis electronics employed in the apparatus of FIG. 1.

Referring now to FIG. 3, the electronic system illustrated there includes a programmable waveform generator 41. The operation of the waveform generator 41 is initiated and controlled by a programmable digital processor 42. A digital signal processor 47 receives the signals generated by the motion sensors (e.g., geophones) 17 and 18 and also the signal generated by the waveform generator 41. A measure of the displacement of the foot 11 is obtained from motion sensor 18. A measure of the force is obtained from the difference of the two sensor (e.g., geophone) signals and the known spring constant of spring 14. In effect, the desired value of the complex mechanical impedance of the soil (seen through the contact with the foot 11) is obtained by a comparison with the known mechanical impedance of the calibrated spring 14.

If the two motion sensors are geophones (i.e., velocity sensors), then the output of the foot sensor 18 can be integrated to obtain foot displacement, and the difference of the outputs of the two sensors 17 and 18 can be integrated to obtain force (within the proportionality constant of the stiffness of the reference spring 14). However, if measurements are determined as a function of frequency, as in one embodiment, the ratio of the difference in sensor outputs to the foot sensor output can be used directly without integration of the sensors signals (because in the frequency domain, integration is equivalent to a 90° phase shift and division by angular frequency, and these operations are common to both the force and foot sensor outputs from sensors 17 and 18, respectively, which are used only in ratio of one to another).

Under the control of processor 42, the waveform generator 41 generates a swept or stepped sinusoidal signal, for example, which progressively varies in frequency over a pre-selected band; e.g., 50 to 150 Hz or 100 to 200 Hz. Also, the rate of change of frequency can also change so that, for constant amplitude, energy content is greater at some frequencies; e.g., at lower frequencies than at other, higher frequencies. This progression is advantageous in improving signal-to-noise ratio as described in greater detail below. The drive signal provided by the waveform generator 41 is applied through a power amplifier 43 to the motor or drive transducer 13.

As mentioned above, the difference between the outputs of the first and second motion sensors 17 and 18 is proportional to the force that is applied to contact foot 11, while the output of the second motion sensor 18 is proportional to soil displacement. A ratio of these values provides a force-to-displacement ratio.

Both of the force and displacement values (or sensor outputs proportional to force and displacement) have real and imaginary components, where the real component is in-phase and the imaginary component is in-quadrature (90° out of phase) with the drive signal provided by waveform generator 41 (or other reference signal). The real component (and also the imaginary component) of the ratio of force-to-displacement can be derived from the real and imaginary parts of the complex valued force and displacement signals derived from sensors 17 and 18. In one embodiment, the measurement of surface stiffness and the derived measurement of shear modulus are based on only the real part of the force-to-displacement ratio.

It has been found that extracting the real component of the force-to-displacement ratio (i.e., "dynamic stiffness") improves the accuracy of the measurement of the shear modulus, as compared, for example, with using the absolute amplitude of the force-to-displacement ratio, since the imaginary component arises largely due to various energy dissipative mechanisms in the complex behavior of soil. Likewise, while measurement at a single frequency would theoretically be possible, the actual behavior of soil has been found to be somewhat frequency dependent. In addition to potential inherent frequency dependency of soil elastic properties, frequency-dependent behavior or resonances may be caused by (a) standing seismic waves caused by reflections from the sides of a road bed or from the sides of a trench where the soil is being compacted; (b) improper contact between the soil and the measurement foot, and (c) the dynamic interaction between a finite sized foot and an elastic half space. Resonance effects or strong frequency excursions due to nearby boundaries can be minimized or removed by averaging the measured data over a wide frequency range, or else by deleting a narrow band of anomalous data from the average. Thus, the preferred embodiment measures over a range of frequencies to improve signal-to-noise ratio and to minimize the impact of the above listed example anomalies in the stiffness versus frequency response.

In one preferred embodiment, the foot diameter and operational frequency band of the signal provided by the waveform generator 41 are chosen so that the ground input reactance does not differ significantly over the measurement band from its static value (i.e., values at zero frequency).

Given the use of a substantial band of measuring frequencies, the signal-to-noise ratio and the resulting final accuracy can be improved if tracking filters are incorporated into the signal processor. Since measurements are made at one frequency at a time, tracking filters can be used to reject noise in the force and displacement signals at all other frequencies.

One technique for implementing such filters is to use FFT processing, stepping the test frequency from one bin to another bin. Another technique is to utilize synchronous detection, making use of a quadrature (i.e. sine and cosine) oscillator to obtain the desired complex ratio of force to displacement. An advantage of the synchronous detector approach is that much of the signal processing can be done utilizing analog computer techniques, substantially reducing the cost of the analog/digital converter and the digital signal processor.

Another advantage of using a substantial range of frequencies is that interference from tonal noise can be more easily excluded from the final determination, either by operator decision to exclude atypical frequency components, or by an automatic expert system as indicated at reference character 48. An example of a tonal source of interfering noise would be a vibrating soil compactor operating in the general vicinity in which the test measurements are taking place.

Figure 8:
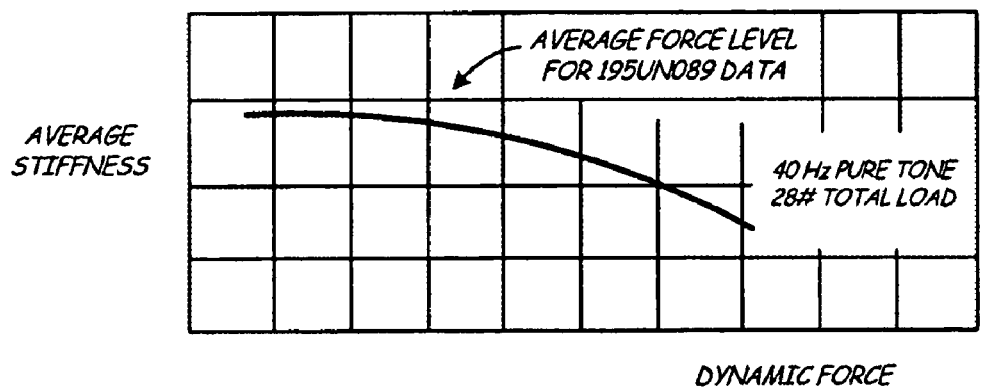
FIG. 8 is a plot of the measured stiffness of compacted soil, showing the measurement error, which can result from using excessively large dynamic force levels.

In order to provide an accurate measurement, the amplitude of the excitation force applied to the shaker motor 13 must be limited to a fairly low level. Otherwise, the measurement process itself can introduce compacting effects or may interfere with the measurement process by causing slippage between adjacent grains of the soil material so that the resultant measurement does not accurately reflect static shear modulus. This effect is illustrated in FIG. 8, where the measured average stiffness of well-compacted "processed gravel" (as might be used as the sub-grade for a highway) is plotted, for a range of dynamic force test levels. Clearly, the poor signal-to-noise ratio, which might exist at a test site where road construction work is in progress cannot be corrected by simply increasing the test force level.

Figure 9:
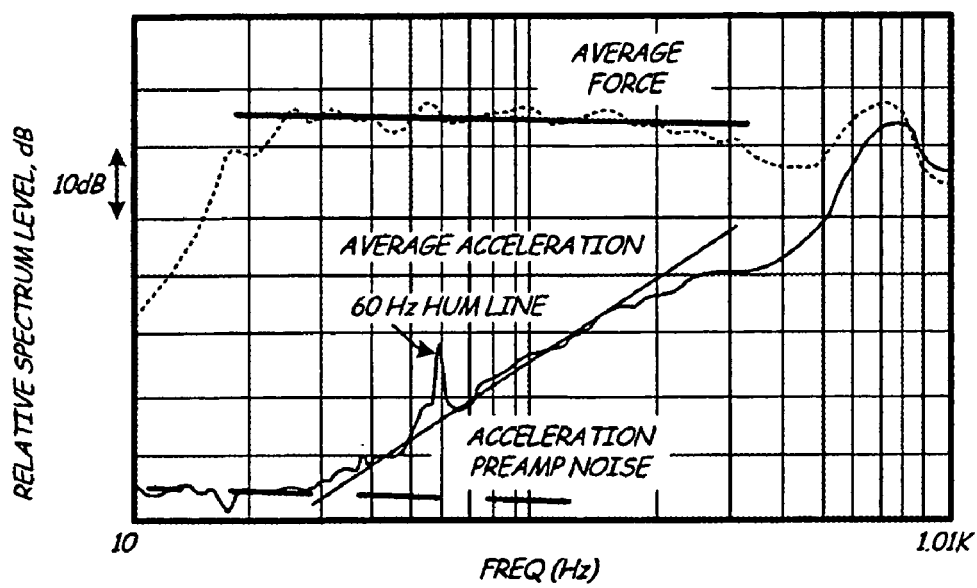
FIG. 9 is a plot of the force spectrum level applied to compacted soil during a field test of its shear modulus, as well as the acceleration spectrum level resulting from the applied force.
Figure 10:
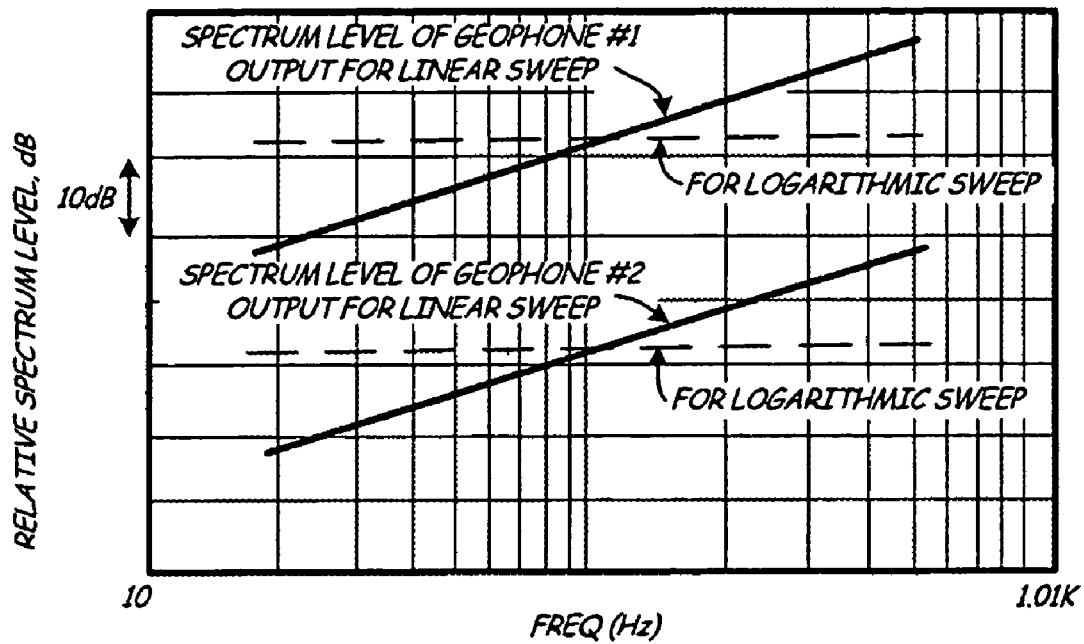
FIG. 10 illustrates the advantage of replacing the accelerometer used for FIG. 9 with a geophone as used in FIG. 1, and the further advantage of using a nonlinear frequency sweep.

FIGS. 9 and 10 illustrate three techniques used in solving the noisy test site problem. FIG. 9 plots measured force and acceleration signal levels on processed gravel at a very quiet test site, using a linear frequency sweep. While the force gauge's signal lies well above its noise floor, the accelerometer's signal is less than the preamp broadband noise at frequencies below about 40 Hz. In addition, a weak hum line at 60 Hz is seen to be about 10 dB above the signal. These measurements were conducted using a commercially available impedance head rather than the instrumentation package illustrated in FIG. 1.

FIG. 10 shows the estimated improvements, first due to substituting a geophone, for the accelerometer used in the commercial impedance head, and then changing the linear sweep to a 20 dB/decade logarithmic sweep, in the 40–400 Hz band (dashed line). That is, the logarithmic frequency sweep spends 10 times as much time in the 40 Hz frequency bin as did the linear sweep; and one-tenth as much time in the 400 Hz bin. In addition, the preamp noise for the low electrical impedance geophone is lower than the preamp noise for the high impedance accelerometer in the commercial head.

While the above two described techniques solve the weak noise problems (e.g., electronic noise), it is clear that much stronger narrow band noise interference (e.g., typical noise due to a rotating weight or oscillating compactor) could be removed by deleting narrow bands from the data. The amount of additional noise reduction provided by a tracking filter will depend on the filter's bandwidth. For example, if the filter is designed to have a constant proportional bandwidth, i.e. a constant Q, then the additional noise reduction should be independent of frequency. For example, a further noise reduction of between 10 and 15 dB is expected for a Q of 10, a significant advantage.

Figure 11:
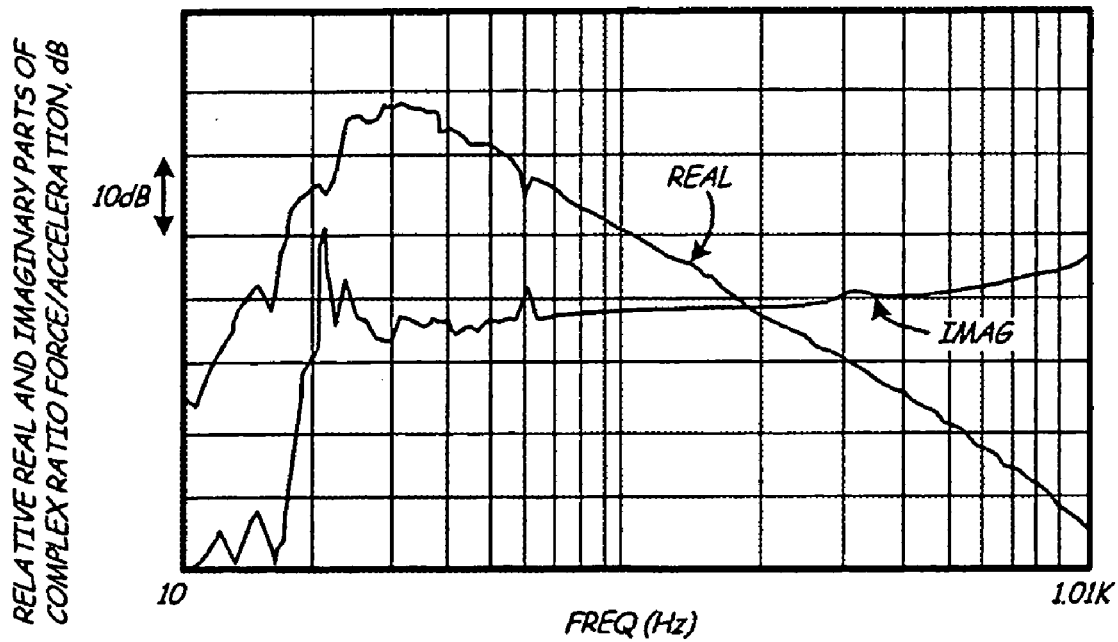
FIG. 11 plots the real and imaginary parts of the complex ratio of the applied force and resulting acceleration signals for FIG. 9.
Figure 12:
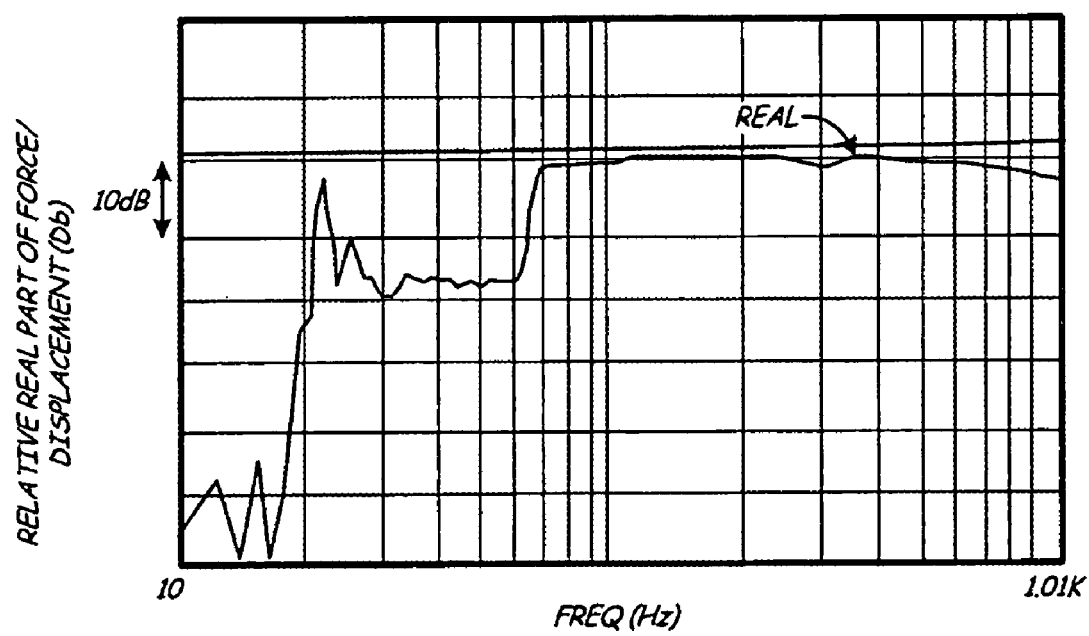
FIG. 12 plots the corresponding real and imaginary parts of the complex ratio of the applied force and the resulting displacement signals.

FIG. 11 plots the complex ratio of force and acceleration, whose power spectra are shown in FIGS. 9 and 10. The plot of the real part (commonly known as a spring line) is seen to be nearly straight. This is shown more clearly in FIG. 12, where the "Real" plot in FIG. 11 has been multiplied by $\omega^2$ in order to obtain the real part of force-to-displacement. The average of the real part of the stiffness, in the 40 to 400 Hz frequency band is about 90,000 lbs/in.

The analytical relationship between the shear modulus of an ideal half space and the normal mechanical stiffness seen by a rigid circular disk rigidly attached to the surface of the half space is, $$K = \frac{4 \cdot G \cdot a}{(1 - v)}$$

where:
  K is the stiffness (e.g., in lbs/in)
  G is the shear modulus (e.g., in lbs/in$^2$,
  a is the radius of the disk (e.g., in inches)
  v is Poisson's Ratio The result for the rigid annular foot 11 has been found to be very nearly the same as for a rigid circular disk. The soil shear modulus inferred by the above equation for the example 90,000 lbs/in measured stiffness, assuming that v=¼, is G=7,600 psi.

The corresponding value of dry density can be estimated from the measured soil stiffness, by using an empirical relationship derived from a large set of field measurements. The mechanical stiffness at each test site was determined using the apparatus of FIG. 1; the dry density was then measured by the sand cone technique. Six different soil types were included in this sampling. The estimated dry density of the soil, which produced FIG. 12 was about 124 lbs/cu ft.

Figure 4:
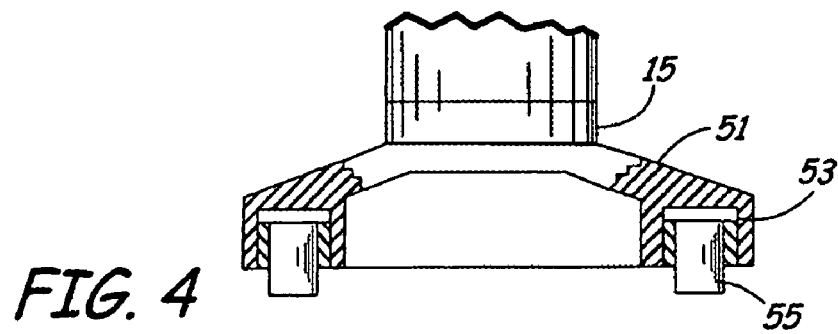
FIG. 4 is a cross-sectional view illustrating an alternate contact foot design.
Figure 5:
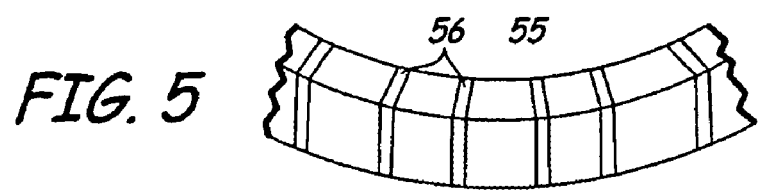
FIG. 5 illustrates a segmented rim employed in the FIG. 4 foot design.
Figure 7:
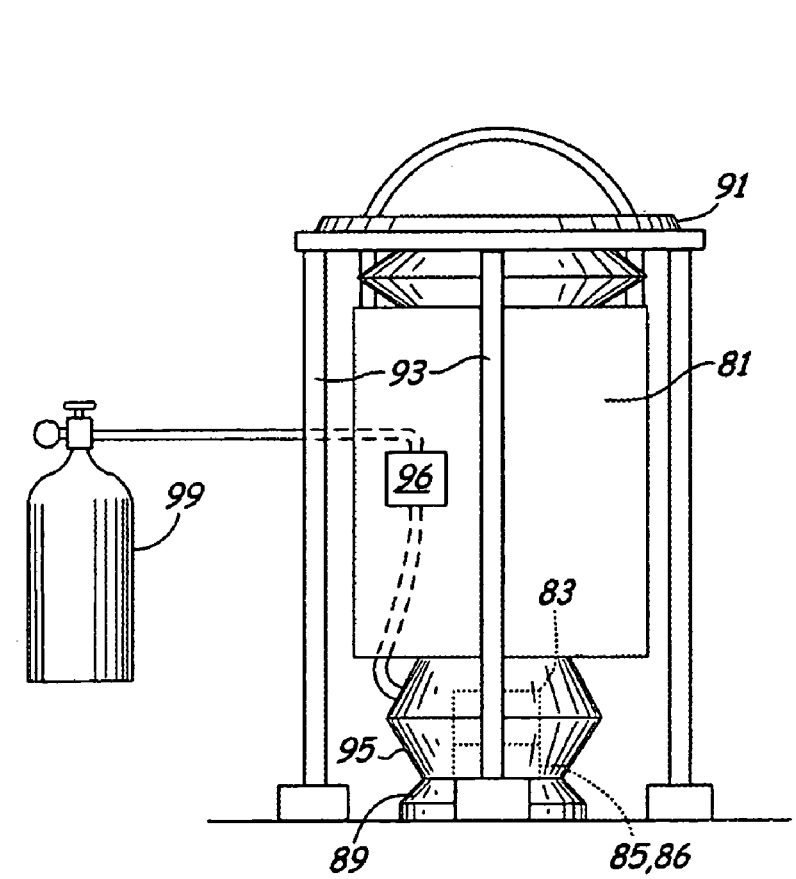
FIG. 7 is a side view of alternate construction of the measurement apparatus providing for automatic variation of bias force.

An alternate construction for contacting the soil in the surface area under the contact foot is illustrated in FIGS. 4 and 5. The concept for the annular foot in FIG. 4 is essentially the same as for the annular foot of FIG. 2, except that the articulated design allows the annular foot to conform to a soil surface, which is not flat. In this construction, the foot housing 51 provides an annular groove 53. Fitting into the groove 53 are a series of thin metal segments 55 coupled together by a high glass transition temperature viscoelastic material such as plasticized polyvinyl acetate or a urethane such as PRC's 1564, whose modulus decreases drastically at frequencies below about 100 Hz. Such a material, designated by reference character 56, forms a structure, which is statically soft so as to conform to soil surface irregularity, but is dynamically rigid so as to transmit vibratory energy. An alternate design to achieve the same result over a wide temperature range would make use of a low durometer low glass transition temperature elastomer such as a silicone rubber for element 56, whose modulus would remain low over a wide temperature range, and thus permit the individual segments to slowly conform to the soil surface irregularity. Dynamic rigidity could be achieved by segmenting volume 53 and then filling it with a fluid such as silicone oil. The individual volumes would be coupled together with small orifices.

Figure 6:
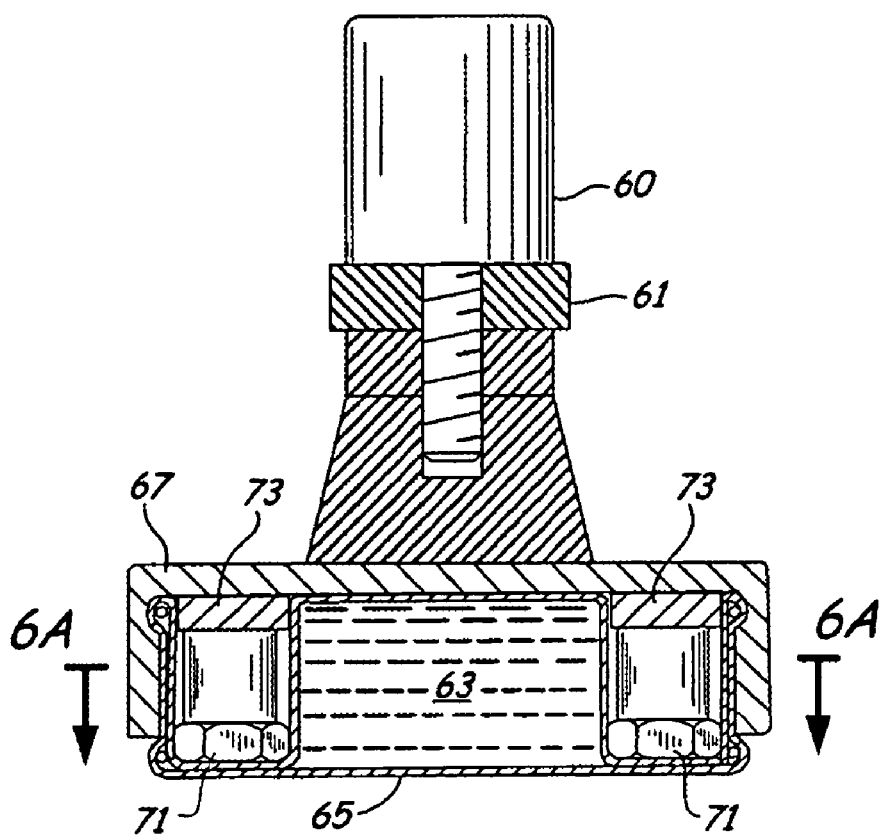
FIG. 6 is a diagram illustrating an alternative construction of contact foot and sensing transducers.
Figure 6A:
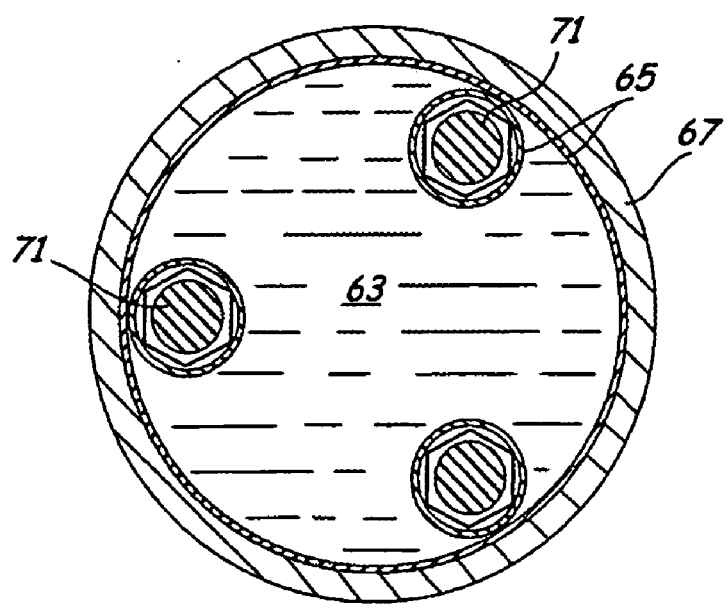
FIG. 6A is a sectional view taken substantially on the line A—A of FIG. 6.

In the embodiment illustrated in FIGS. 6 and 6A, the output of the shaker motor or transducer 60 is coupled to the soil through a force gauge 61 and an oil filled cavity 63 which is defined between top and bottom membranes of a flexible bladder 65 set into a cup-shaped foot 67. The bladder 65 includes a series of pockets, separate from the cavity 63, into which are placed a series of three motion sensors 71. Foam spacers 73 isolate the motion sensors from the vibratory motion of the foot so that they effectively measure only the motion of the soil.

Advantages of this design are the that the lower flexible membrane would apply normal stress to a larger area than would the foot of FIG. 2 or of FIG. 4, and that the membrane should conform to an irregular soil surface much better than would the foot of FIG. 2, and even better than the foot of FIG. 4.

While the bladder is susceptible to puncture, this is dealt with by the fact that three geophones are in contact with the soil's motion without actually being inside the bladder. Likewise, dynamic pressure inside the rubber bag is sensed from outside the bag by the force gauge 61 shown in FIG. 6. Thus, an inadvertent cut in the membrane could quickly be remedied by snapping a spare bladder into place.

It is well known that the modulus of soils depends on the effective static stress. The weight of the devices shown in FIG. 1 and FIG. 2 would be chosen to produce a known, typical stress in the soil beneath the foot (reference character 11). To further improve accuracy of measurement, multiple scans of varying frequency excitation may be performed at different levels of downward bias force, i.e. overburden. It is advantageous that the change in bias force be provided automatically. In the embodiment illustrated in FIG. 7, a housing 81 contains the batteries and electronics, separate from the shaker motor 83 and the sensing transducers 85 and 86, which are coupled to the contact foot 89. Coupled to the housing 81 is a frame 91 having a plurality of feet 93, which contact the ground at spaced locations around the contact foot 89. An air spring 95 selectively couples downward force from the housing 81 to the contact foot 89 in accordance with the pressure within the air spring. A tank 99 of compressed air provides a source of air for selectively pressurizing the air spring. Solenoid valves 96, operated under the control of the programmable digital processor incorporated in the electronics package, are provided for selectively venting or filling the air spring. As an alternative, weights could be manually added in a preselected progression to an instrument package such as that illustrated in FIG. 1.

In view of the foregoing it may be noted that the embodiments discussed above provide for the in-situ measurement of soil properties, which allows accurate and repeatable measurements of the stiffness and shear modulus of a surface layer of soil. These measurements can be used as indicators of the state of compaction of the soil. The apparatus can be easily and quickly operated. The apparatus can be easily transported to a construction site and moved between successive measurement positions at the site. The apparatus is highly reliable and is of relatively simple and inexpensive construction.

It should also be noted that a calibrated applied force gauge (of various types) and a calibrated foot motion sensor may be used as an alternative to employing two identical motion sensors and a calibrated spring. In this example, the shaker motor applies force to the contact foot directly, without an intervening spring. The calibrated force gauge is attached between the shaker motor and the contact foot to measure the dynamic force applied to the contact foot. The calibrated foot motion sensor measures foot and hence ground motion.

2. Measurement in Motion

Compaction measurement devices, such as the one described above, can be implemented on a moving platform for making one or more measurements along the direction of motion. Measurement while in motion uses a tracked or wheeled vehicle or a walking mechanism, and the vehicle can be self propelled, towed or pushed. A frame that moves with the vehicle places one or more measurement devices in contact with the ground for the time that is required to make a valid measurement. Several alternative embodiments are described below.

a. Rolling Contact

In one embodiment, the circular planar disk or annulus foot contact (such as foot 11 in FIG. 1) of the measurement device can be replaced with a contact foot formed as an effectively rigid roller. The dynamic force from the measurement device is applied to the roller axle and the dynamic response of the ground is measured at the roller axle or other suitable location.

FIG. 13 illustrates a schematic view of a moving platform 200 in which a compaction measurement instrument 202 is mounted on one or more rolling wheels 204 for contacting and moving over ground 206. In this illustrative figure, ground 206 has a soil foundation 208 covered by a layer of pavement 210 and a void in the soil under the pavement. This figure illustrates the additional use of the instrument for assessing elastic properties and structural integrity of pavements including the detection of voids in the soil foundation under pavements.

Compaction measurement instrument 202 can include one or more of the measurement devices shown and discussed with reference to FIGS. 1–12 or any other compaction measurement device. Measurement instrument 202 generates a dynamic excitation force 212, which is applied to the axle 214 of wheel 204. A sensor, such as motion sensor 18 in FIG. 1, measures the vertical motion of wheel 204 in response to the excitation force 212 to obtain the stiffness of ground 206 under wheel 204. As described above, the instrument itself can include one or more sensors for measuring the force applied to axle 214, or the sensor package on axle 214 can have the capability to measure applied force as well as vibratory response. In a similar manner as discussed above, the data processing translates the dynamic force 212 at axle 214 to force applied to ground 206 by compensating for the force drop across the mass of roller 204, based on directly measured or inferred roller acceleration.

As described above, the measurements of both applied vibratory force and resultant vibratory motion are processed within instrument 202 to measure ground stiffness and thereby infer ground modulus. Also, the inferred modulus can be obtained, as discussed above, from a model or experimental calibration of the wheel/ground interaction.

Wheel 204 is an effectively rigid roller. Some degree of compliance around the wheel, such as by a slightly compliant tire 216, can be used to mitigate motion induced wheel vibration and provide a consistent quality of ground contact. As is understood by persons skilled in the art, compliance between the stiffness measurement instrument and the soil reduces the apparent surface stiffness and reduces the sensitivity of the instrument to changes in soil stiffness. Thus, the compliance around wheel 204, if any, is selected to be sufficiently stiff relative to expected maximum vales of ground stiffness so that the measurement accuracy is not intolerably degraded. Alternatively, the compliance around wheel 204 is sufficiently well know that it can be compensated for in the data processing algorithms that estimate ground stiffness from the sensor outputs, such as the outputs from sensors 17 and 18 in FIG. 1 The resulting measurement during forward motion is a spatial average in the direction of wheel travel, with the averaging length, L, determined by, averaging length,$L$=(measurement time duration,$T$)·(platform speed of advance,$V$)

In one embodiment, the diameter and width of wheel 204 are selected to optimize ground contact and minimize noise induced by vibration of the roller passing over a non-uniform surface.

A single shaker in measurement device 202 provides spatial samples separated by the averaging length, L, or a running average of ground properties with averaging length L. For each sample, the device provides a continuous spatial coverage along the line of forward motion, wherein the measurement time is limited by the size of the area to be averaged in the direction of forward motion and the desired speed of advance. Alternatively, platform 200 can be moved between samples and be stationary during each measurement. Multiple side-by-side measurement devices 202 can be used to conduct concurrent measurements along parallel tracks.

The moving platform 200, which carries measurement device 202 and the rolling contact wheel 204 can operate under its own propulsive power or can be towed (i.e., be a trailer) or pushed by another vehicle such as truck or compactor. The platform can include an integrated positioning system, such as a global positioning system (GPS) or other type of system, and automatic data logging. The data logging elements and associated memory can be implemented within device 202 or as a separate device on or off of platform 200.

FIG. 14 is a schematic diagram, which illustrates a moving platform 220 according to an alternative embodiment of the present invention. The same reference numerals are used in FIG. 14 as were used in FIG. 13 for the same or similar elements. In this embodiment, compaction measurement device 202 is attached to a rigid shoe 224 having an external rolling belt/track 226. When platform 220 moves relative to ground 206, belt 226 rolls around rigid shoe 224, as guided by wheels or slides 228. Rigid shoe 224 and belt 226 expand the contact area of measurement device 202 with ground 206 relative to the rolling wheel shown in FIG. 13.

b. Plant-and-Place Mechanisms

In other embodiments, a plant-and-place mechanism is used to enable the measurement device to be stationary with respect to the ground for some duration while the platform carrying the measurement device maintains continuous forward motion. In general, plant-and-place mechanisms are more complex than rolling contact mechanisms, but have the potential advantages of allowing a longer time duration measurement, measuring a fixed segment of soil and not "smoothing" or "averaging over" localized defects, avoiding rolling contact vibration and noise, and a higher probability of consistent contact with the ground.

A number of plant-and-place mechanisms can be used. Examples include a tracked platform, an overhead suspension rail/track, and a walkingmechanism. Other mechanisms can also be used. Again, the vehicle or platform on which the measurement devices can be self-propelled, towed or pushed.

i. Tracked Platform

FIG. 15 is a schematic diagram illustrating a side view of a tracked vehicle platform 230, according to one embodiment of the present invention. FIG. 16 is a front-end view of platform 230. Platform 230 includes one or more endless tracks or belts 232, which are mounted for rotation around idler wheels or rollers 234 and 236 during movement of the platform relative to ground 206. Track 232 extends along a closed-loop path around wheels 234 and 236, which has an elongated segment 233 for engaging track 232 with ground 206. Wheels 234 and 236 support track 232 at opposite ends of the closed-loop path and are separated from one another along a direction of motion of platform 230 by a distance that defines the length of the elongated segment 233 that engages ground 206.

Platform 230 can include a tow bar 238 for attaching the platform as a trailer to a vehicle (such as a truck or compactor) and pulling platform 230 in the direction of arrow 240. Alternatively, platform 230 can include its own propulsion system or be pushed. For example, platform 230 or any of the other platforms disclosed in the various figures, can include a self-propulsion mechanism 242 such as an engine, a motor or other device. Propulsion mechanism 242 can drive one of the drive wheels 234 or 236 or another element or wheel on the platform, for example.

One or more measurement devices 202 are installed on track 232 for movement with the track along the closed-loop path. Each measurement device 202 comes in contact with ground 206, through track 232, when it passes under the bottom of the forward idler wheel 234 and leaves the ground as it passes the rear wheel 236. In this embodiment, each measurement device 202 provides a dynamic force that drives ground 206 through track 232 such that the track or belt forms a contact foot of the device. The total length of track determines the spatial sampling rate for a single stiffness measurement device. As illustrated in FIGS. 15 and 16, denser spatial sampling can be attained using additional stiffness measurement devices attached to track 232.

Maintenance of each measurement device 202 in a fixed position relative to the ground 206 is possible because the segment of track 232 that contacts the ground does not move relative to the ground. As a result, the measurement device does not move relative to the ground for the duration of time between lay-down by the front wheel 234 and pick-up by the rear wheel 236. Measurements can also be made when platform 230 is stationary, if desired.

With multiple devices 202 operating concurrently, mutual interference between the devices can degrade performance for long duration waveforms. However, mutual interference, even for long duration test signals, can be mitigated by a) staggering the initiation times of the drive signals to the various measurement devices; and b) using different distinguishable waveforms (ideally orthogonal to one another) for each of the multiple devices, together with matched filtering. Therefore, each device can avoid interference from other devices by filtering the drive signals and resulting ground response signals generated by other devices.

The dwell time and hence maximum measurement averaging time for the tracked platform 230 shown in FIGS. 15 and 16 is determined by the ratio of the length of track between the idler wheels 234 and 236 (the "reach" of the track) and the rate of advance of platform 230. The appropriate dwell/averaging time depends on the force level applied and measurement noise (i.e., signal-to-noise ratio). However, measurement devices 202 preferably remain in a fixed position on the ground 206 for a time duration sufficient to make a stiffness or, more generally, surface input impedance measurement while platform 230 maintains forward motion. Therefore, the speed of vehicle advance along ground 206 and the length of the track 232 are selected to achieve the desired measurement duration for a single instrument. This implies, track length,$L$=(measurement time duration,$T$)·(platform speed of advance,$V$)

where the track length, L, refers to the distance between centers of the track end wheels 234 and 236.

A single shaker in a measurement device 202 will provide spatial samples that are separated by approximately the distance, 2L+nD, where D is the diameter of the track end wheels 234 and 236. Multiple side-by-side tracks 232 may be used to conduct concurrent measurements along parallel tracks. The tracked platform 230 can include an integrated positioning system, such as a global positioning system (GPS) or other type of system, and automatic data logging.

ii. Overhead Suspension

Figure 17:
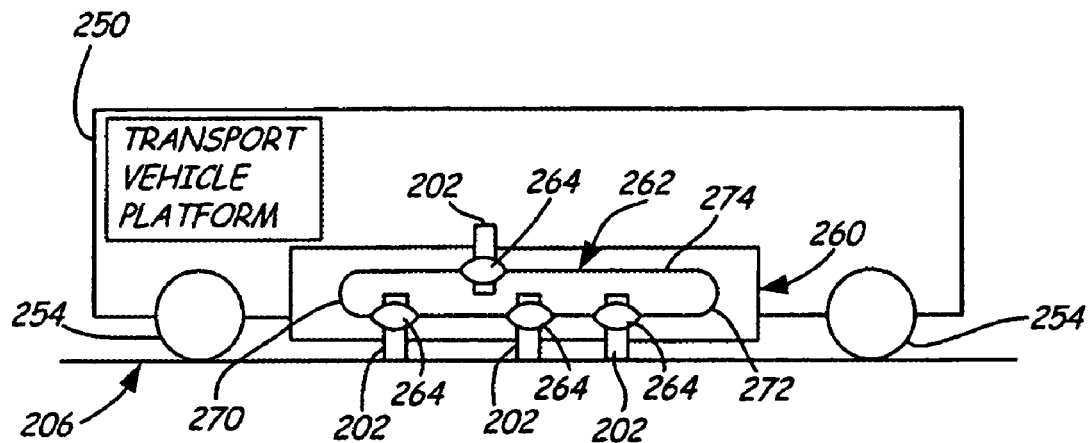
FIG. 17 is a schematic diagram of a vehicle platform in which one or more measurement devices move along a guide, according to an alternative embodiment of the present invention.

In another embodiment shown in FIG. 17, one or more measurement devices 202 are carried by their "heads, rather than by their "feet." In this embodiment, a transport vehicle platform 250 includes wheels 252 and 254 for allowing movement of platform 250 relative to ground 206. Platform 250 has a frame 260 that moves with the platform and places one or more measurement devices 202 in contact with ground 206 for the time required to make a valid measurement while the platform is in motion.

In one embodiment, frame 260 is rigidly attached to platform 260. In this case the measurement device or devices 202 move within frame 260 such that they maintain a fixed position relative to ground 206 during the measurement period. The frame 260 includes a guide 262 to control the motion of the devices 202 within the frame. Guide 262 may be in the form of a groove, a track, a rail attached to the frame or other means understood by those skilled in the art. Guide 262 defines a closed-loop path.

Each measurement device 202 is attached to guide 262 through a suitable attachment 264. This attachment can be made at any suitable location on the device 202 such that the device is sufficiently supported in frame 260 and the contact foot of the device can be placed in stationary contact with the ground during the measurement period and then removed from the ground following the measurement period. The stiffness measurement devices 202 are movable along the closed-loop path defined by guide 262 relative to the platform.

If more than one measurement device 202 is used, the devices can be linked by a chain or wire that ensures that the relative spacing between devices is maintained along guide 262. The motion of a measurement device within frame 260 can be controlled by a separate drive linked to the platform drive that ensures that the relative velocity of the device with respect to the platform is such that the device remains stationary with respect to ground 206 while the measurement is being made. Alternatively, in the case where multiple measurement devices are employed, a drive mechanism may not be required since when a device contacts the ground it will remain attached to the ground in that location until some means along guide 262 lifts the device off of the ground.

As the platform moves forward, such as from right to left in FIG. 17, a measurement device passes around the curved segment 270 at the left end of guide 262 and comes in contact with ground 206 where it remains in contact with the ground at a stationary position on the ground until it is lifted from the ground as it passes around the semicircular segment 272 of guide 262 at the opposite, right end. It then travels along the upper segment 274 of guide 262 until it encounters the original semicircular segment. The path is then repeated. During ground contact, measurement device 202 transmits a dynamic excitation force to ground 206 through a contact foot, such as foot 11 shown in FIG. 1 and receives the resulting dynamic response from the ground.

The speed of vehicle advance and the length of guide 262 are selected so that the measurement device 202 remains stationary on ground 206 for the duration of time needed for a single measurement, for example. This implies, guide length,$L$=(measurment time duration,$T$)·(platform speed of advanced,$V$)

A single shaker will therefore provide spatial samples separated by approximately a distance 2L. Multiple measurement devices 202 can be used to provide denser spatial sampling in the direction of platform motion. Multiple side-by-side guides 262 can be used to conduct concurrent measurements along parallel tracks.

As with the other embodiments, platform 250 can include an integrated positioning system, such as a global positioning system (GPS) or other type of system, to provide the frame location and an integrated or remote processor to locate the specific measurements and to gather, organize, store, analyze, validate, and/or output the data.

iii. Walking Mechanism

In another embodiment, one or more measurement devices are placed on the "shoe" of any type of implementation of a plant-and-place walking mechanism. While the platform moves forward at a rate of progression over the ground, the shoe and thus the measurement devices on the shoe remain in stationary contact with the ground for the amount of time necessary to make a measurement. A walking mechanism utilizes a walking mechanism to move in a manner similar to a human walking, where each foot does not move relative to ground for the period of a pace. There are numerous types of walking mechanisms many of that are used in robotics or in toys, any of which can be adapted to carry one or more measurement devices in accordance with the present invention.

Figure 18:
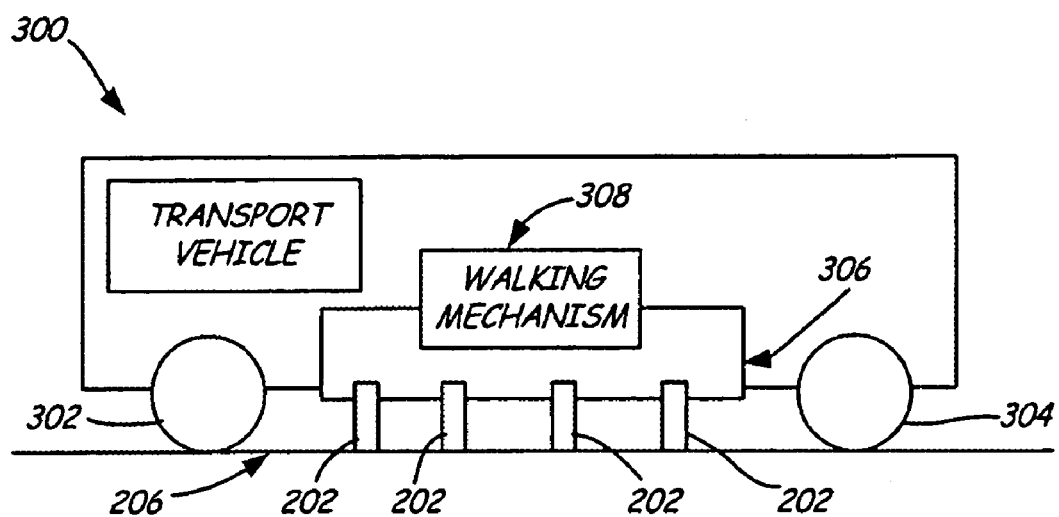
FIG. 18 is a schematic view of a vehicle platform having a walking mechanism according to an alternative embodiment of the present invention.

FIG. 18 is a side, schematic view of a vehicle platform 300 having a walking mechanism according to one embodiment of the present invention. In this embodiment, platform 300 includes wheels 302 and 304, frame 306, walking mechanism 308 and one or more measurement devices 202. Frame 306 rigidly supports measurement devices 202 and articulates with respect to platform 300 through walking mechanism 308. Walking mechanism 308 allows frame 306 to remain stationary on ground 206 for the measurement period at one position (as shown in FIG. 17) and then to lift and step to a new stationary position on the ground as vehicle platform 300 advances along the ground. The motion of frame 306 is synchronized with the motion of platform 300.

The walking mechanism formed by frame 306 ensures consistent contact of devices 202 with ground 206 and remains in a single location for the duration of measurement. The dwell time for the walking mechanism concept is determined by walking mechanism 308 and the rate of advance. The appropriate dwell/averaging time depends on the force level applied and measurement noise. Multiple feet and shoes can be used to increase the spatial sampling density.

The above-described embodiments allow soil property measurements to be made while the platform on which the measurement device or instrument is supported remains in continuous motion relative to the ground. For example, in the rolling contact embodiments shown in FIGS. 13 and 14, the measurement is made through a rolling contact where the measurement device actually moves relative to the ground over the duration of the measurement. Rolling contact can be established by a wheel or cylindrical roller or by a tracked belt. A tracked belt provides more ground contact area and likely better control of contact over that area than the limited contact of a wheel. The rolling contact method measures the soil property continuously in space. A set of contiguous spatial sample intervals are obtained, with each interval length being determined by the time duration of the measurement times the speed of advance, where each measurement represents an average over the spatial length of that interval.

In other embodiments, soil property measurements are made through plant-and-place mechanisms. For example, the measurement device is supported on a rail, track or beam so that the device is stationary relative to the ground for the duration of the measurement, even though the platform is maintaining continuous forward motion. This method makes soil property measurements over a set of spatially sampled discrete points. The sampling interval is determined by the spacing of devices on the rail, track or beam if multiple devices are used, or by the length of the rail, track or beam if a single instrument is carried by the mobile platform.

As various changes could be made in the above constructions and operations without departing from the scope of the invention, it should be understood that all matter contained in the above description or shown in the accompanying drawings shall be interpreted as illustrative and not in a limiting sense. Workers skilled in the art will recognize that changes may be made in form and detail without departing from the spirit and scope of the invention. For example, embodiments of the present invention are not restricted to the particular measurement devices described with reference to FIGS. 1–12. Other types of measurement devices and movement mechanisms can also be used.

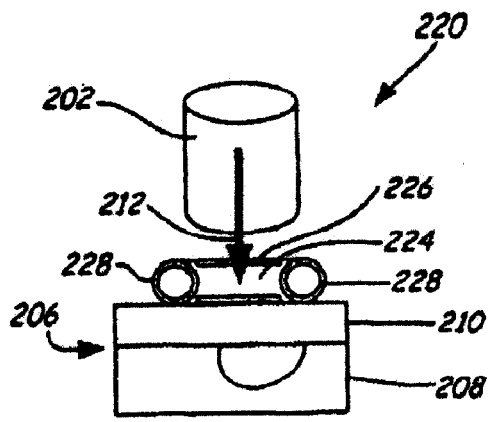

What is claimed is:

1. An apparatus for the in-situ measurement of the stiffness of a surface, the apparatus comprising:
   a platform, which is movable relative to the surface; and
   a stiffness measurement device supported by the platform in a stationary position relative to the surface for a measurement period during continuous movement of the platform along the surface.

2. The apparatus of claim 1 wherein:
   the platform comprises an endless track extending along a closed-loop path and having an elongated segment for engaging the surface; and
   the stiffness measurement device is mounted to the track so as to be movable with the track along the closed-loop path.

3. The apparatus of claim 2 wherein the track forms a contact foot of the stiffness measurement device.

4. The apparatus of claim 2 wherein:
   the stiffness measurement device generates a dynamic force and is mounted to the track such that the dynamic force is applied to the surface through the track, and a dynamic response of the surface is received by the measurement device through the track.

5. The apparatus of claim 2 wherein the platform further comprises first and second wheels, which support the track at opposite ends of the closed-loop path and are separated from one another along a direction of motion of the platform by a distance that defines a length of the elongated segment that engages the surface.

6. The apparatus of claim 2 and further comprising:
   a plurality of stiffness measurement devices, including the first mentioned measurement device, mounted to the track and having fixed positions relative to one another along the track.

7. The apparatus of claim 2 and further comprising:
   a plurality of endless tracks, including the first mentioned guide, which extend generally parallel to one another along a respective closed-loop path; and
   at least one stiffness measurement device mounted to each of the plurality of endless tracks so as to be movable along the respective closed-loop paths relative to the platform.

8. The apparatus of claim 1 wherein:
   the platform comprises a guide defining a closed-loop path; and
   the stiffness measurement device is mounted to the guide so as to be movable along the closed-loop path relative to the platform, wherein the path comprises a segment along which the guide places the stiffness measurement device in contact with the surface at the stationary position relative to the surface for the measurement period.

9. The apparatus of claim 8 and further comprising:
   a plurality of stiffness measurement devices, including the first mentioned measurement device, mounted to the guide and having fixed positions relative to one another along the closed-loop path.

10. The apparatus of claim 8 and further comprising:
    a plurality of guides, including the first mentioned guide, wherein each guide defines a respective closed-loop path; and
    at least one stiffness measurement device mounted to each of the plurality of guides so as to be movable along the respective closed-loop path relative to the platform.

11. The apparatus of claim 1 wherein
the platform comprises a frame, which articulates relative to the platform;
the stiffness measurement device is rigidly mounted to the frame; and
the platform comprises a walking mechanism, which places the frame on the surface in the stationary position for the measurement period and then steps the frame to a new stationary position on the surface as the platform advances along the surface.

12. An apparatus for the in-situ measurement of the stiffness of a surface, the apparatus comprising:
a platform, which is movable relative to the surface;
a rigid shoe supported by the platform and having an external rolling belt that travels along a closed-loop path and has an elongated segment for engaging the surface; and
a stiffness measurement device, which generates a dynamic force and is mounted to the rigid shoe such that the dynamic force is applied to the surface through the rigid shoe and the rolling belt, and the device receives a dynamic response from the surface through the rigid shoe and the rolling belt.

13. The apparatus of claim 12 wherein the platform further comprises first and second wheels, which support the rolling belt at opposite ends of the closed-loop path and are separated from one another along a direction of motion of the platform.

14. The apparatus of claim 12 and further comprising:
a further rigid shoe supported by the platform and having a respective external rolling belt that travels along a respective closed-loop path and has a respective elongated segment for engaging the surface; and
a further stiffness measurement device, which generates a respective dynamic force and is mounted to the further rigid shoe such that the respective dynamic force is applied to the surface through the further rigid shoe and the respective rolling belt, and the device receives a respective dynamic response from the surface through the further rigid shoe and the respective rolling belt.

15. A method of making an in-situ measurement of the stiffness of a surface, the method comprising:
(a) moving a platform relative to the surface;
(b) carrying a stiffness measurement device on the platform;
(c) supporting the stiffness measurement device in a stationary position relative to the surface for a measurement period during movement of the platform along the surface;
(d) applying a vibratory force from the stiffness measurement device to the surface; and
(e) sensing motion of the surface in response to the vibratory force and generating a respective measurement signal, which is representative of the surface stiffness.

16. The method of claim 15 wherein:
step (b) comprises supporting the stiffness measurement device on an endless track extending along a closed-loop path and having an elongated segment for engaging the surface;
step (c) comprises moving the stiffness measurement device with the track along the closed-loop path such that the device remains in the stationary position relative to the surface along the elongated segment; and
steps (d) and (e) comprise applying the vibratory force and sensing the motion of the surface through the track.

17. The method of claim 15 wherein:
step (b) comprises supporting the stiffness measurement device along a guide defining a closed-loop path; and
step (c) comprises moving the stiffness measurement device along the closed-loop path relative to the platform, wherein the path comprises a segment along which the guide places the stiffness measurement device in contact with the surface at the stationary position relative to the surface for the measurement period.

18. The method of claim 15 wherein:
step (b) comprises supporting the stiffness measurement device rigidly on a frame carried by the platform; and
step (c) comprises articulating the frame relative to the platform so as to place the frame on the surface in the stationary position for the measurement period and then step the frame to a new stationary position on the surface as the platform advances along the surface.

19. An apparatus for the in-situ measurement of the stiffness of a surface, the apparatus comprising:
a platform, which is movable relative to the surface;
a roller supported by the platform for engaging the surface; and
a stiffness measurement device, which generates a dynamic force and is mounted to the roller such that the dynamic force is applied to the surface through the roller, and the device receives a dynamic response from the surface through the roller, wherein the device comprises a set of one or more sensors, the set having an output representative of the dynamic force applied to the roller and an output representative of the dynamic response of the surface.

20. The apparatus of claim 19 wherein the stiffness measurement device comprises a circuit for translating the dynamic force applied to the roller into force applied to the surface by compensating for a force drop across the mass of the roller, based on directly acceleration of the roller.

* * * * *

UNITED STATES PATENT AND TRADEMARK OFFICE
CERTIFICATE OF CORRECTION

PATENT NO. : 7,073,374 B2  Page 1 of 1
APPLICATION NO. : 10/901639
DATED : July 11, 2006
INVENTOR(S) : Evan F. Berkman It is certified that error appears in the above-identified patent and that said Letters Patent is hereby corrected as shown below:

Column 18
Line 54, insert --claim 21. The apparatus of claim 19 wherein the roller comprises a wheel having an axle, and wherein the stiffness measurement device is coupled to the axle such that the device applies the dynamic force to the axle and receives the dynamic response of the surface through the axle.--

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,073,374 B2  Page 1 of 2
APPLICATION NO. : 10/901639
DATED : July 11, 2006
INVENTOR(S) : Evan F. Berkman It is certified that error appears in the above-identified patent and that said Letters Patent is hereby corrected as shown below:

Delete the title page and substitute therefore the attached title page showing the corrected number of claims in printed patent.

Column 18
Line 54, insert --claim 21. The apparatus of claim 19 wherein the roller comprises a wheel having an axle, and wherein the stiffness measurement device is coupled to the axle such that the device applies the dynamic force to the axle and receives the dynamic response of the surface through the axle.--

This certificate supersedes the Certificate of Correction issued April 20, 2010.

Signed and Sealed this

Eleventh Day of May, 2010

David J. Kappos
*Director of the United States Patent and Trademark Office*

CERTIFICATE OF CORRECTION (continued)

(12) United States Patent
Berkman

(10) Patent No.: US 7,073,374 B2
(45) Date of Patent: Jul. 11, 2006

(54) SOIL COMPACTION MEASUREMENT ON MOVING PLATFORM

(75) Inventor: Evan F. Berkman, Newton Center, MA (US)

(73) Assignee: BBNT Solutions LLC, Cambridge, MA (US)

(*) Notice: Subject to any disclaimer, the term of this patent is extended or adjusted under 35 U.S.C. 154(b) by 0 days.

(21) Appl. No.: 10/901,639

(22) Filed: Jul. 29, 2004

(65) Prior Publication Data

US 2005/0022585 A1 Feb. 3, 2005

Related U.S. Application Data

(60) Provisional application No. 60/491,180, filed on Jul. 30, 2003.

(51) Int. Cl.
*B23Q 17/20* (2006.01)

(52) U.S. Cl. .................................................. 73/78
(58) Field of Classification Search .................. 73/78
See application file for complete search history.

(56) References Cited

U.S. PATENT DOCUMENTS

| | | | |
|---|---|---|---|
| 1,871,756 A | 8/1932 | Spath | 73/594 |
| 3,224,253 A | 12/1965 | McKay | 73/594 |
| 3,362,216 A | 1/1968 | Hardin et al. | 73/594 |
| 3,427,877 A | 2/1969 | Swift et al. | 73/146 |
| 3,481,183 A | 12/1969 | Swift | 73/573 |
| 3,643,498 A | 2/1972 | Hardin | 73/594 |
| 3,693,513 A * | 9/1972 | Borsutzki et al. | 404/117 |
| 3,778,177 A * | 12/1973 | Haker et al. | 73/654 |
| RE27,875 E | 1/1974 | Swift | 73/67.1 |
| 3,795,286 A | 3/1974 | Meyer | 73/594 |
| 3,813,929 A | 6/1974 | Hardin et al. | 73/784 |
| 3,863,202 A | 1/1975 | Landrum, Jr. | 73/594 |
| 3,924,451 A | 12/1975 | Drnevich | 73/67.3 |
| 3,946,598 A | 3/1976 | Towne et al. | 73/594 |
| 4,127,351 A * | 11/1978 | Vural | 404/72 |
| 4,149,253 A | 4/1979 | Paar et al. | 404/84 |
| 4,348,901 A | 9/1982 | Vural et al. | 73/594 |
| 4,382,384 A | 5/1983 | Mitchell et al. | 73/594 |
| 4,445,378 A | 5/1984 | Zuckerwar | 73/594 |
| 4,467,652 A | 8/1984 | Thurner et al. | |
| 4,589,288 A * | 5/1986 | Porter et al. | 73/849 |
| 4,594,899 A | 6/1986 | Henke et al. | 73/784 |
| 4,655,082 A | 4/1987 | Peterson | 73/594 |
| 4,722,635 A * | 2/1988 | Schnell | 404/76 |
| 4,738,138 A | 4/1988 | Redman-White | 73/594 |
| 4,750,157 A | 6/1988 | Shei | 73/594 |
| 4,870,601 A * | 9/1989 | Sandstrom | 702/43 |
| 4,912,979 A | 4/1990 | Sondergeld et al. | 73/594 |
| 4,918,988 A | 4/1990 | Ebihara et al. | 73/594 |
| 4,995,008 A | 2/1991 | Hornbostel et al. | 73/594 |

(Continued)

OTHER PUBLICATIONS

"Compaction Monitor", Product Brochure, Gas Research Institute, Foster-Miller, Inc. and Longyear, pp. 1-3 (Jan. 18, 1994).

(Continued)

*Primary Examiner*—Max Noori
(74) *Attorney, Agent, or Firm*—Westman, Champlin & Kelly

(57) ABSTRACT

An apparatus and method are provided for the in-situ measurement of the stiffness of a surface. The apparatus includes a platform, which is movable relative to the surface. A stiffness measurement device is supported by the platform in a stationary position relative to the surface for a measurement period during movement of the platform along the surface.

21 Claims, 9 Drawing Sheets